United States Patent [19]
Appel et al.

[11] 4,193,991
[45] Mar. 18, 1980

[54] CANINE PARVOVIRUS VACCINE

[75] Inventors: Max J. G. Appel; Leland E. Carmichael, both of Ithaca, N.Y.

[73] Assignee: Cornell Research Foundation, Inc., Ithaca, N.Y.

[21] Appl. No.: 971,296

[22] Filed: Dec. 20, 1978

[51] Int. Cl.$^2$ .............................................. A61K 39/12
[52] U.S. Cl. ...................................... 424/89; 435/238
[58] Field of Search ...................... 424/89; 195/1.1–1.7

[56] References Cited

PUBLICATIONS

Binn, L. N. et al., Infection and Immunity 1(5):503–508 (1970), Recovery and Characterization of a Minute Virus of Canines.
Eugster, A. K. et al., Southwestern Vet. 30(1):59–60 (1977), Diarrhea in Puppies:Parvovirus–Like Particles Demonstrated in Their Feces.
Siegl, G., "The Parvoviruses" in Virology Monographs #15, p. 71 (1976), Springer-Verlag, Wien, NY.
Storz, J. et al., Am. J. Vet. Res. (AJVRA)33(1):269–272 (1972), Distribution of Antibodies Against Bovine Parvovirus 1 in Cattle and Other Animal Species.

*Primary Examiner*—Shep K. Rose
*Attorney, Agent, or Firm*—Jones, Tullar & Cooper

[57] ABSTRACT

The present invention relates to the method of protecting dogs against canine parvoviruses. More specifically, the present invention relates to a method of producing an inactivated (killed) canine parvoviral vaccine from a native virulent strain of CPV for use as a vaccine in dogs against disease caused by virulent canine parvoviruses.

6 Claims, No Drawings

CANINE PARVOVIRUS VACCINE

Parvoviruses are characterized as small animal DNA viruses consisting of an isometric protein capsid and a short molecule of single-stranded DNA. Although parvoviruses have been recovered and isolated from various animals, there had been no definite isolation of a pathogenic canine parvovirus until now (Siegl, *The Parvoviruses*, Springer-Verlag, New York 1976). Bachmann et al. include the dog as a possible parvovirus host in a report detailing the characteristics of parvoviruses in general (Bachmann et al., *Intervirology* 10: in press, 1978). In 1970, Binn et al. reported the recovery and characterization of a "minute virus of canines" (Binn et al., *Infect. Immun.* 1: 503, 1970). The isolates described were of canine origin, however, their pathogenicity was not known, and cytopathic effect (CPE) was produced in only a very narrow host range, i.e. only in a single continuous canine cell line, and not in primary canine nor primary or continuous cell cultures from other species. Pathogenicity for dogs was not determined nor was evaluation of vaccine potential done. Based on known properties of the Cornell isolates, it is clear that the recent CPV isolates are not the same as the "minute virus of canines" as described by Binn. In 1977, Eugster and Nairn reported a circumstantially-suggested causative link between diarrhea in puppies and a canine parvovirus. (Eugster, Nairn, *Southwestern Veterinarian*, 30: 59, 1977). The isolate reported therein could not be serially propagated in MDCK cells, the only cell line tested. Again, pathogenic potential was unexamined and no experimental animal inoculations were performed. In 1978, widespread outbreaks of an apparently new disease in canines appeared (Appel, Cooper, Greisen and Carmichael, *JAVMA* 173(11) 1516–1518; December 1978), occurring in both the United States and Australia (unpublished). The natural disease is characterized by diarrhea, fever, and leukopenia (relative lymphopenia).

The principal object of this invention is to provide a vaccine for the protection of dogs against canine parvoviral disease.

Another object of the present invention is to provide a method of preparing such a vaccine from a strain of parvovirus that can be propagated in primary cells derived from canine and feline species as well as in several established cell lines from various species.

Other objects will be apparent as the description proceeds.

The isolate recovered is Cornell type strain 780916 (referred to as CPV916). The strain was recovered from the feces and intestinal tract samples of composite specimens submitted for diagnosis from the Argonne National Laboratories on Sep. 9, 1978. Aggregates of the canine parvovirus (CPV) were detected by electron microscopy. The fecal material was partially purified by differential ultracentrifugation and diluted in Medium 199 plus Gentamicin (50 mg/ml). Various non-oncogenic cell cultures were inoculated with this material at the time of cell passage. Several additional CPV strains, with indistinguishable properties, have been isolated by the methods above, which have similar immunogenic characteristics. The results of cell passage are shown in Table I.

Table 1

| CELL TYPE | CYTOPATHIC EFFECT (Passage No. -days) | HEMAGGLUTININ PRODUCTION (Pig RBC) | TYPE CPE FA = immunofluorescence, specific* |
|---|---|---|---|
| Primary feline kidney | ± (1–4 days) | + | IN inclusions; + FA |
| Feline lung cell line(FLC) | + (1–5 days) | + | Gross degeneration, + FA rounding, IN inclusions |
| Mink lung cell line | ± (3 days) | + | + FA, indistinct inclusions |
| Primary canine kidney | + (6 days) | + | Rounding, degeneration failure to re-grow, + FA |
| Second, third passaged canine kidney | + (6–7 days) | + | Rounding, degeneration failure to re-grow, + FA |
| A72/WRCC (canine fibroblast) | + (2–5 days) | + | Cell rounding, failure to re-grow, + FA, indistinct inclusions (granular) |
| Maden-Darby canine kidney | + (4–6 days) | + | Cellular degeneration. IN, inclusions indistinct, + FA |
| Vero (African Green Monkey) | + (6–8 days) | + | Cellular degeneration |
| Bovine fetal spleen cells | None | + | None, + FA |

*Although specific fluorescence with *canine parvovirus* antiserum conjugate was recorded here, fluorescent antibodies prepared with the closely-related feline panleukopenia virus also was used, providing identical results. The canine and feline viruses are indistinguishable serologically.

Viral growth in the various cell lines and in primary cells from canine and feline species was unexpected in light of the reports of Binn et al., and Eugster and Nairn, above. It was found that a favorable growth occurred in primary feline and canine kidney cells as well as in several cell lines including the mink lung cell line (MLCL, ATCC #CCL 64; mvl Lu(NBL-7). It is to be expected that other cell lines or primary cells from other canine tissue sites or other species also would support growth, although they are as yet untested.

Production of CPV vaccine.

CPV 916 strain was used as seed for vaccine preparation. The cell substrate from any of the non-oncogenic primary or established cell cultures listed in Table I may be used. For experimental studies, primary canine kidney and MLCL cultures were employed. At the time of cell seeding, CPV was inoculated with a high multiplicity of infection into the culture. Virus and cells were allowed to mix and infected cells were then seeded at an appropriate concentration (about 1:3 dilution) in a non-inhibitory medium optimal for each cell type. Infected cells were allowed to grow out, together with uninoculated controls, and were incubated at about 35° C.–37° C. for 5 days in a serum medium (for example, MEM+10% FCS). Cells then were incubated for an additional two days in a non-serum medium (for example, MEM or Eagles+LAH 0.5%). The cells were frozen at −70° C. and thawed rapidly three times to disrupt the cells. Ultrasonic treatment may also be used. Culture fluids were clarified by centrifugation at 500×g for 20 minutes. At this point, the virus harvests were tested for infectivity and hemagglutination (HA) titers. The virus grown in MLCL (CCL-64) cells had an infectivity of $10^{5.0}$ TCD$_{50}$/ml. HA titers were greater than 1024. The virus grown in canine renal cells had infectivity of $10^{5.5}$ TCD$_{50}$/ml and HA of 2048.

The virus was inactivated by adding formalin (37% formaldehyde), 1:400, to the clarified tissue culture in a tightly stoppered bottle with a magnetic stirrer. The mixture was placed in an incubator at 37° C. and mixed well for 48 hours. It was found that the vaccine in the crude form caused no local or systemic reactions in the dogs. Concentrations of formalin, ranging from 0.05 to 0.25 percent, have been found acceptable. Other methods of inactivation, e.g. beta-propio lactone, also may be used in appropriate concentrations by those skilled in the art.

Since the vaccine will be unsatisfactory if any virus is present, it must be tested for residual virus. For this purpose, 0.1 ml of stock 35% sodium bisulfite, diluted 1:2 in PBS, was added to each 5 ml of vaccine. The formalin was removed by dialyzing against PBS, pH 7.2 for 24 hours. To test for virus, 0.5 ml amounts were inoculated into 10 tubes and incubated for 8 days. The presence of virus in inoculated test cultures was tested by hemagglutination tests or fluorescent antibody (FA) tests for viral growth. None was detected.

Hemagglutination (HA)/Hemagglutination Inhibition (HI) tests for CPV

Hemagglutination tests were performed in microtiter plates (Cooke Engineering, Microbiological Associates, Cat. #18-007) at 2° C.–4° C. with 1.0% pig erythrocytes (PRC) at pH 7.4 using a method similar to that described by Johnson, R. H. and Cruickshank (1966)(Problems in classification of feline panleukemia virus, Nature (London) 212: 622–623). The highest dilution of antigen in 0.025 ml giving 2+ HA with 0.05 ml PRC was the endpoint. For the HA-HI tests sera were treated with receptor-destroying enzyme (RDE)(Microbiological Associates, Cat. #30899). If isoagglutinins in the canine test serum were greater than 1:80 it was found necessary to first absorb the serum with 0.1 ml of 50% packed PRC. Serum dilutions commenced at 1:80 and 2-fold serial dilutions then were made using 0.025 ml microdiluters. Antigen (0.025 ml) diluted to contain 4–8 units of HA was added and the mixtures were incubated for one hour at room temperature. The PRC suspension was added, mixed, and the test was incubated at 2° C.–4° C. for 2–4 hours before reading. The highest dilution of serum inhibiting HA by 4–8 units of virus (usually 8 units) was considered the endpoint. The titer was expressed as the reciprocal of the endpoint dilution.

Vaccine trials

The vaccine was administered as an aqueous suspension either in adjuvant (Alhydrogel; Al(OH)$_3$) or without adjuvant. A dose of 1 cc was given intramuscularly (IM). A second dose was given 9–10 days later, after the first antibody response was noted. Antibody responses were measured by HA-HI tests, as described above. Experimental specific pathogen-free beagle dogs were challenged intravenously (IV) ten days later with $10^{4.0}$ TCD$_{50}$ of virulent CPV. Because the experimental disease is milder than the field cases, in most instances, criteria for illness were elevated temperatures and/or relative lymphopenia, the latter being the most consistent sign.

EXAMPLE 1

The results of vaccination with a non-adjuvanted, inactivated CPV vaccine prepared by propagation in the MLCL cell line are shown in Table 2. All dogs vaccinated with the inactivated CPV had marked serological responses and were fully protected against the challenge inoculum. Control dogs were found susceptible (non-immune), as evidenced by clinical signs of fever and/or lymphopenia.

Table 2

Canine Parvovirus Vaccination

Expt. A: Inactivated homotypic virus vaccine

Serology (Hemagglutination inhibition 1/titer)

| Treatment Dog | Vaccination 1 10-4 (pre-vacc.) | Vaccination 2 10-13 (post-vacc. 1 day 9) | Virulent virus** challenge 10-20 (post-vacc. 2 day 16) | 10-25 (post-chall. day 5) | 10-27 (post-chall. day 7) | Response to challenge |
|---|---|---|---|---|---|---|
| A78-25 0* | Neg.+ | 320 | 6,400 | 3,200 | 3,200 | I**** |
| /1* | Neg. | >5,120 | 3,200 | 1,600 | 1,600 | I |
| /2* | Neg. | >5,120 | 3,200 | 1,600 | 1,600 | I |
| /3* | Neg. | >5,120 | 6,400 | 3,200 | 3,200 | I |
| /4* | Neg. | >5,120 | 6,400 | 6,400 | 6,400 | I |
| /5*** | Neg. | Neg. | Neg. | 800 | 6,400 | S |
| /6*** | Neg. | Neg. | Neg. | 800 | 6,400 | S |
| /7* | Neg. | >5,120 | 25,600 | 6,400 | 6,400 | I |
| /8* | Neg. | >5,120 | 25,600 | 6,400 | 3,200 | I |
| /9* | Neg. | 2,560 | 12,800 | 6,400 | 6,400 | I |
| /10* | Neg. | 2,560 | 51,200 | 6,400 | 6,400 | I |

*Inactivated (0.5% formalin) canine parvovirus:
mink cell passage 3:  10-4-78  ⎫ Infectivity titer $10^{5.0}$ Prior to
mink cell passage 4:  ⎬ inactivation. HA titer = 1024 pre- and
10-13-78 ⎭ post-inactivation.
**virulent virus ($10^4$TCD$_{50}$ CPV;iv)  10-20-78 - challenge virus.
***non-vaccinated controls:
challenge as above  10-20-78
+<1:80
****I = Immune; S = Susceptible: illness characterized by fever, leukopenia, relative lymphobpenia or other signs.

EXAMPLE 2

The results of vaccination with a CPV vaccine prepared by propagation in primary dog kidney cells are shown in Table 3. Again, all vaccinated dogs were fully protected. No difference in the responses to adjuvanted versus aqueous (non-adjuvanted) vaccines were observed.

Table 3

Canine Parvovirus Vaccination

Expt. B: Inactivated homotypic virus vaccine

| Treatment Dog | Vaccination Pre-vacc. | Serology (Hemagglutination inhibiton 1/titer) (Post-vacc. 6 days) | (Post-vacc. 17 days | Virulent virus** challenge (Post-chall. 5 days) | (Post-chall. 7 days) | Response to challenge*** |
|---|---|---|---|---|---|---|
| 800C* (A) | Neg.⊕ | 3,200 | 3,200 | 6,400 | 6,400 | Immune |
| 801C* (A) | Neg. | 800 | 6,400 | 6,400 | 6,400 | Immune |
| 802C* | Neg. | 1,600 | 6,400 | 12,800 | 6,400 | Immune |
| 803C* | Neg. | 6,400 | 25,400 | 6,400 | 3,200 | Immune |
| 804C* | Neg. | >6,400 | 12,800 | 12,800 | 12,800 | Immune |
| A78-26/10 Control | Neg. | Neg. | Neg. | 1,600 | 800 | Not immune |
| A78-26/13 Control | Neg. | Neg. | Neg. | 3,200 | 3,200 | Not immune |

*Inactivated (0.25% formalin, 48h, 37° C., pH 7.2)
Dog parvovirusDog kidney-cell-passaged virus ($10^{5.5}$ infectivity titer; 1:2048 hemagglutination titer) prior to inactivation.
(A) indicates dog given vaccine plus $AL(OH)_3$ adjuvant.
**Virulent virus ($10^4$ $TCD_{50}$ CPV: iv)
⊕<1:80
***Illness characterized by fever, leukopenia, relative lymphopenia or other signs.

The peripheral white blood cell and lymphocyte counts of the vaccinated and control dogs are shown in Table 4. None of the vaccinated animals developed elevated temperatures, or other signs, in contrast to the control animals. The most prominent and consistent sign in the experimental controls was a reduction in circulating lymphocytes (relative lymphopenia), even when leukopenia was not marked.

Table 4

Canine Parvovirus Vaccination

Inactivated homotypic virus vaccine

Peripheral blood WBC and lymphocyte counts

| | Status | Pre-challenge WBC(a) | L(b) | 3 days post-chall. WBC | L | 4 days postchall. WBC | L | 5 days post-chall. WBC | L | 7 days post-chall. WBC | L |
|---|---|---|---|---|---|---|---|---|---|---|---|
| A78-25/0 | Vacc. | 9.4 | 4.1 | 11.3 | 3.2 | 12.7 | 3.3 | 10.8 | 2.7 | 11.3 | 3.8 |
| /1 | Vacc. | 11.4 | 4.3 | 14.5 | 3.7 | 15.7 | 6.3 | 11.9 | 3.1 | 15.9 | 5.1 |
| /2 | Vacc. | 20.3 | 6.2 | 13.4 | 4.8 | 14.5 | 5.2 | 8.3 | 4.0 | 13.7 | 4.4 |
| /3 | Vacc. | 15.5 | 4.0 | 12.3 | 6.5 | 11.0 | 5.9 | 11.9 | 5.9 | 12.2 | 6.6 |
| /4 | Vacc. | 13.0 | 4.2 | 17.2 | 6.2 | 15.0 | 6.3 | 12.1 | 6.7 | 16.0 | 9.7 |
| /5 | Control | 22.5 | 8.1 | 15.9 | 2.5 | 23.6 | 4.4 | 10.6 | 5.5 | 12.9 | 5.9 |
| /6 | Control | 18.6 | 5.9 | 25.6 | 2.0 | 16.5 | 3.0 | 15.2 | 3.9 | 9.3 | 3.6 |
| /7 | Vacc. | 11.8 | 4.2 | 11.9 | 4.2 | 10.7 | 4.5 | 14.3 | 4.4 | 12.8 | 3.6 |
| /8 | Vacc. | 15/4 | 4.2 | 13.4 | 5.1 | 12.9 | 3.9 | 20.0 | 7.2 | 12.1 | 5.0 |
| /9 | Vacc. | 11.1 | 3.7 | 9.1 | 4.6 | 11.1 | 4.6 | 9.7 | 3.9 | 10.4 | 4.0 |
| /10 | Vacc. | 11.0 | 3.5 | 10.7 | 2.9 | 14.4 | 3.3 | 14.7 | 4.1 | 10.2 | 2.9 |
| Cl | Vacc. | 18.2 | 4.9 | 20.2 | 6.1 | 9.4 | 2.3 | 16.0 | 3.8 | 13.5 | 2.8 |
| C2 | Vacc. | 9.6 | 3.2 | 19.1 | 8.2 | 13.3 | 4.0 | 16.5 | 3.6 | 12.8 | 4.1 |
| C3 | Vacc. | 10.6 | 3.9 | 10.3 | 3.6 | 10.5 | 4.4 | 16.7 | 4.6 | 11.9 | 4.8 |
| C4 | Vacc. | 15.7 | 3.1 | 10.2 | 3.8 | 9.4 | 3.4 | 8.8 | 3.0 | 11.7 | 4.7 |
| C5 | Vacc. | 13.9 | 4.7 | 10.4 | 3.3 | 13.9 | 4.1 | 15.9 | 5.2 | 15.4 | 3.7 |

(a)Total white blood cell count $\times 10^3$
(b)Total lymphocyte count $\times 10^3$ The Cornell type strain 780916 (CPV 916) is on deposit and can be obtained from the James A. Baker Institute for Animal Health, New York State College of Veterinary Medicine at Cornell University, Ithaca, New York.

The isolation of the CPV 916 strain of parvovirus and its propagation in primary cells and in cell lines of various species such as mink lung cells and canine kidney cells represent a distinct advance in the art. The isolation of CPV 916 is not only the first definite isolation and propagation in vitro of a novel and distinct pathogenic canine parvovirus, but it supplies a method of vaccinating dogs against virulent CPV.

We claim:

1. The method of protecting dogs against virulent canine parvovirus which comprises inoculating an animal with inactivated canine parvovirus vaccine prepared in accordance with a process which comprises the steps of growing a strain of canine parvovirus in a non-oncogenic cell culture and then inactivating the virus.

2. The method of claim 1 where the inactivation is accomplished by adding formalin to the cell culture.

3. The method of claim 1 where the cell culture consists of mink lung cell line.

4. The method of claim 1 where the cell culture consists of primary canine kidney cells.

5. The method of claim 1 where the strain of canine parvovirus used is CPV 916.

6. The method of claim 5 where the cell culture consists of mink lung cell line and the inactivation is accomplished by adding formalin to the cell culture.

* * * * *